(12) United States Patent
Morrison et al.

(10) Patent No.: US 6,433,068 B1
(45) Date of Patent: *Aug. 13, 2002

(54) HYDROCARBON GELS AS SUSPENDING AND DISPERSING AGENTS AND PRODUCTS

(76) Inventors: David S. Morrison, 23 Grey Birch Pl., The Woodlands, TX (US) 77381; Lin Lu, 2100 Tanneyhill, Apt. 2009, Houston, TX (US) 77008; Robert H. Ray, 13445 Ella Blvd. #813, Houston, TX (US) 77014

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/007,838

(22) Filed: Jan. 15, 1998

Related U.S. Application Data

(60) Provisional application No. 60/033,811, filed on Mar. 7, 1997.

(51) Int. Cl.[7] .............................................. C08L 53/00
(52) U.S. Cl. .................... 524/505; 524/47; 524/420; 524/430; 524/431; 524/432; 524/445; 524/449; 524/451; 424/59
(58) Field of Search .................................. 524/575, 505, 524/47, 420, 430, 431, 432, 445, 449, 451; 424/59

(56) References Cited

U.S. PATENT DOCUMENTS

| | | | | |
|---|---|---|---|---|
| 5,221,534 A | | 6/1993 | DesLauriers et al. | 424/78.03 |
| 5,558,872 A | | 9/1996 | Jones et al. | |
| 5,840,338 A | * | 11/1998 | Roos et al. | 424/488 |
| 6,026,527 A | * | 2/2000 | Pearce | 5/654 |

FOREIGN PATENT DOCUMENTS

| | | |
|---|---|---|
| WO | WO 94/12190 | 6/1994 |
| WO | WO 97/29842 | 8/1997 |
| WO | WO 97/31623 | 9/1997 |

* cited by examiner

*Primary Examiner*—Peter D. Mulcahy
(74) *Attorney, Agent, or Firm*—Arthur M. Dula

(57) ABSTRACT

Hydrocarbon gels comprising from about 0.1 to about 50 percent on a weight. basis of diblock, triblock, multiblock and/or radial block copolymers based on synthetic thermoplastic rubbers or mixtures, in a mixture with a hydrocarbon, one or more hydrocarbon-soluble substances, or mixtures thereof, which are useful as suspending or dispersing agents for solids and/or liquids.

18 Claims, No Drawings

HYDROCARBON GELS AS SUSPENDING AND DISPERSING AGENTS AND PRODUCTS

CROSS REFERENCE TO RELATED APPLICATIONS

This application claims the priority of Provisional Application Serial No. 60/033,811, filed Mar. 7, 1997.

FIELD OF THE INVENTION

The invention relates to heterophase, thermally reversible hydrocarbon gels which are suitable for use as suspending and dispersing agents. The suspending and dispersing agents of the invention employ a hydrocarbon gel which contains block copolymers, the copolymers being preferably derived from styrene-rubber block units.

BACKGROUND OF THE INVENTION

Various types of gel products are known in the art. U.S. Pat. No. 5,221,534 of Applicants' Assignee, for example, discloses gel compositions which contain one or more health and beauty aid components wherein the gel comprises a hydrocarbon oil and a blend of at least two different polymers selected from the group consisting of diblock and triblock polymers. The hydrocarbon oils disclosed in this patent are indicated as having characteristics which would cause them to remain liquid at temperatures ranging from 0° C. up to about 200° C. for almost all applications.

U.S. Pat. No. 4,164,563 to Chang discloses compositions for topical application to the skin which are indicated as being greasy occlusive viscous bases comprising a mixture of from 40–90% of a greasy viscous base and from 10–60% of a solid non-irritating ointment forming powder. Other ingredients such as colorants can also be included in the composition. The composition can also contain a thickening agent which can be an unvulcanized elastomeric block polymer.

U.S. Pat. No. 5,221,534 discloses gels comprising a mineral oil and blends of copolymers and including health and beauty aid components.

PCT Patent Application No. WO88/00603 of Francis et al. describes block copolymer compositions which are described as gels or gelloid liquid extended polymer compositions which comprise an intimate mixture of a block copolymer containing relatively hard blocks and relatively elastomeric blocks. A suitable block copolymer is Kraton 1651, a triblock copolymer. The copolymer additionally contains at least 500 parts by weight of extender liquid per 100 parts of the block copolymer, the liquid being present to extend and soften the elastomeric blocks of the block copolymer.

European Patent Application No. 224389 of Gamarra et al. discloses styrene-diene block copolymer compositions and in particular a mixture of triblock copolymers and a hydrocarbon oil. These compositions are useful as sealing materials.

U.S. Pat. No. 4,369,284 describes a transparent gel prepared from triblock copolymers and oils useful as molded products. The triblock copolymers used therein receive specific styrene end blocks to ethylene and butylene center blocks. The end block to center block ratio is given as being between 31:69 and 40:60.

SUMMARY OF THE INVENTION

It is accordingly one object of this invention to provide heterophase, thermally reversible hydrocarbon gel compositions that have advantageous properties when used as a vehicle to suspend or disperse solids and liquids therein.

A further object of the invention is to provide hydrocarbon gel compositions formed with certain diblock, triblock, radial block and/or multiblock copolymers which have advantageous properties when used as a suspension agent for various solids and non-hydrocarbon liquids.

Other objects and advantages of the present invention will become apparent as the description of the invention proceeds.

In satisfaction of the foregoing objects and advantages, the present invention provides in one embodiment, a thickened and gelled hydrocarbon having solids and/or liquids suspended therein. The thickened and gelled hydrocarbon composition comprises:

(a) from about 20 to about 95 weight percent of a hydrocarbon, and optionally one or more hydrocarbon-soluble substances;

(b) from about 0.1 to about 50 weight percent of a diblock, triblock, radial block and/or multiblock copolymers, or blends thereof comprising from about 0 to about 100 weight percent of one or more diblock copolymers and from about 100 to about 0 weight percent of one or more triblock, radial block and/or multiblock copolymer; and (c) from about 0.01 to about 75 weight percent of one or more solids and/or non-hydrocarbon liquids suspended therein.

The hydrocarbon used in the composition preferably has a vapor pressure up to about 600 mm Hg at 20° C.

DETAILED DESCRIPTION OF THE INVENTION

The present invention is directed to new thickened and gelled hydrocarbon-containing, block copolymer gels having solids and/or non-hydrocarbon liquids suspended or dispersed therein. The gel compositions of the invention comprise a hydrocarbon, optionally one or more hydrocarbon-soluble substances, one or more diblock copolymers, one or more triblock, radial block and/or multiblock copolymers, or a mixture thereof, and one or more solids or liquids suspended or dispersed therein.

The invention may accordingly be described as a gelled and thickened hydrocarbon comprising:

(a) from about 20 to about 95 weight percent of a hydrocarbon, optionally containing one or more hydrocarbon-soluble substances, or mixtures thereof;

(b) from about 0.1 to about 50 weight percent of a diblock, triblock, radial block and/or multiblock copolymers, or a blend thereof comprising from about 0 to about 100 weight percent of one or more diblock copolymer and from about 100 to about 0 weight percent of one or more triblock, radial block and/or multiblock copolymer; and (c) from about 0.01 to about 75 weight percent of one or more solids and/or non-hydrocarbon liquids suspended or dispersed therein.

In a preferred composition of the invention, the copolymers or blends thereof comprise from about 0.1 to about 25 weight percent, preferably from about 0.1 to about 10 weight percent, of one or more triblock, radial block and/or multiblock copolymers and from about 70 to about 99.9 weight percent of one or more diblock copolymers.

When formed into gels, the copolymers or blends thereof comprise from about 0.1 to about 50 weight percent of the total weight of the composition. Preferably the total weight of polymer contained in the hydrocarbon oil will range from about 0.5 to about 30 weight percent, more preferably 1 to 20 weight percent, though this preference may change depending upon the particulars of the application desired, as will be apparent to one skilled in the art.

The gel compositions of the invention are generally non-aqueous. However, water may be added to certain compositions to form emulsions, for example, for use as a spray, cream or lotion.

Each of the diblock, triblock, radial block and/or multi-block copolymers used in the invention contains at least two thermodynamically incompatible segments. By the expression thermodynamically incompatible with respect to the polymers, it is meant that the polymer contains at least two incompatible segments, for example, at least one hard and one soft segment. In general, in a triblock polymer, the ratio of segments is one hard, one soft, one hard or an A-B-A copolymer. Diblock copolymers, on the other hand, are of the A-B type and sequential with respect to hard and soft segments. The multiblock and radial block copolymers can contain any combination of hard and soft segments, provided that there are both hard and soft characteristics. These copolymers are fully disclosed in U.S. Pat. No. 5,221,534, the disclosure of which is incorporated herein by reference.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure for the triblock copolymer is the above-mentioned linear ABA block type; styrene-butadiene-styrene (SBS) and styrene-isoprene-styrene (SIS), which is the Kraton® D rubber series.

A second polymer of this general type is the Kraton® G series. This copolymer comprises a styrene-ethylenebutylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the hydrocarbon or hydrocarbon mixture (the D series polymers having unsaturation within the rubber block).

The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber. The ABA structure of the Kraton® rubber molecule has polystyrene endblocks and elastomeric midblocks.

A preferred triblock polymer is a triblock polymer of the Kraton® G type, in particular Kraton® G-1650. Kraton® G-1650 is an SEBS triblock copolymer which has a specific gravity of about; 0.91, and is said to have a tensile strength of about 500 psi as measured by ASTM method D-412-tensile jaw tester separation speed 10 in/min. The styrene to rubber content of Kraton® G-1650 is said by the manufacturer to be about 29:71, and the Brookfield viscosity is about 8000 (toluene solution, cps at 77° F., 25%w). The Shore A hardness is about 75.

The diblock polymers include the AB type such as styrene-ethylenepropylene (S-EP) and styrene-ethylenebutylene (S-EB), styrene-butadiene (SB) and styrene-isoprene (SI). A preferred diblock copolymer is Kraton® G-1702.

When formed into gels, the hydrocarbon, optionally one or more hydrocarbon-soluble substances, or mixtures thereof, comprises from about 20 to about 95 weight percent of the total weight of the composition. Preferably the total weight of the hydrocarbon, one or more hydrocarbon-soluble substances, or mixtures thereof, contained in the composition will range from about 65 to about 95 weight percent, and more preferably will range from about 70 to about 93 weight percent. Most preferably the total weight of the hydrocarbon, one or more hydrocarbon-soluble substances, or mixtures thereof in the composition of the invention is about 50 weight percent, though this preference may change depending upon the particular application desired, as will be apparent to one skilled in the art.

While not being limited by theory, it is believed that generally the shorter carbon chain length of the hydrocarbon, one or more hydrocarbon-soluble substances, or mixtures thereof, the more volatile is the hydrocarbon. According to the invention, the hydrocarbon, one or more hydrocarbon-soluble substances, or mixtures thereof, is believed to act as a suspending agent or dispersant for the solid or liquid suspended or dispersed in the composition. Thus, when choosing a hydrocarbon, optionally including one or more hydrocarbon-soluble substances, for use in the invention, care must be taken to ensure that the hydrocarbon, or optionally one or more hydrocarbon-soluble substances, is of sufficient chain length to become suitably entwined with the polymer blend, such that a desired gel consistency can be obtained for the particular application intended. Under these considerations, hydrocarbon components useful in the practice of the invention are generally preferred to comprise at least about 5 carbon atoms, preferably at least 8 carbon atoms, and less than about 60 carbon atoms, and which may also contain one or more functional groups selected from the group consisting of hydroxyl, carboxylic acid and carboxylic acid esters.

The hydrocarbons useful in the gels of the invention as defined above include, but are not limited to mineral oils, mineral solvents, mineral spirits, petroleum, waxes, synthetic hydrocarbons (oils and volatile solvents), animal oils, vegetable oils, and mixtures of these hydrocarbons. A preferred hydrocarbon for use in the invention is a white mineral oil sold by Penreco, a subsidiary of Pennzoil Products Company, under the tradename Drakeol.

As noted, there may also be incorporated into the hydrocarbons one or more hydrocarbon-soluble substances such as esters, waxes, petrolatums, resins, mixtures thereof, or the like. Substances of this type may be included in the compositions in amounts of up to about 50 wt.%, based on the total weight of the composition.

The gels of the invention are eminently suitable as suspending and dispersing agents for solids and liquids. It has been discovered that the gel compositions of the invention keep solids and liquids substantially uniformly suspended (evenly dispersed) in numerous applications over substantial periods of time. The solids and liquids may be suspended or dispersed in the gel in amounts of up to 75 wt.%, preferably about 1 to 60 wt.%.

The solids or liquids to be suspended or dispersed in the gel comprises any solid or non-hydrocarbon oil liquid which will disperse into the gel and remains substantially suspended or evenly dispersed therein.

Examples of solids which can be suspended in the gels of the invention comprise zinc oxide, coated zinc oxide, surface-treated zinc oxide, titanium dioxide, coated titanium dioxide, surface-treated titanium dioxide, phosphorescing substances such as fluorescents, molybdenum oxide (a glow-in-the-dark additive available commercially under the tradename Luminova from United Mineral & Chemical), zinc sulfide, copper doped zinc sulfide, graphite, explosive materials, pesticides, herbicides, fungicides, air-sensitive chemicals or reagents, moisture-sensitive chemicals or reagents, boron nitride, iron oxides, talc, mica, plastics, polymers and polymeric materials, silica, silicon dioxide, aluminum oxide, inorganic materials, organometallic compounds, metal particles, phosphorescent or fluorescent materials, medical materials such as antibacterials, antibiotics, antimicrobials, antifungals, and anesthetics, glass, clays, gums, capsules containing various ingredients, starch, modified starches and mixtures thereof.

These applications include, but are not limited to, cosmetics (e.g., pigmented makeups, sunscreens containing physical sunblocks such as titanium dioxide and zinc oxide), agricultural uses (e.g., pesticides, fungicides, herbicides, etc.), and veterinary uses (e.g., dewormers, vaccines, other medicines).

Examples of oil-insoluble liquids which can be suspended in the gels of the invention comprise water, water containing one or more water-soluble materials, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and mixtures thereof.

In a preferred embodiment, the, gels can be hydrocarbons, optionally containing one or more hydrocarbon-soluble substances (such as esters, waxes, petrolatums, resins). The gels comprise the hydrocarbon, one or more diblock copolymers, one or more triblock, radial block and/or multiblock copolymers, or a mixture thereof, and optionally one or more suspended substances. The total polymer content should be from about 0 to 50 wt.%. The gels may be stabilized with suitable stabilizers and/or preservatives, such as vitamin E or BHT. The final products may be anhydrous or emulsions of oil and water. In both cases, the gels provide exceptional stability.

The gel consistency of the invention is controlled by varying the amount, ratio and types of certain polymers, preferably diblock, triblock, radial block and/or multiblock copolymers. The amount of each copolymer and the amount of the mixture contained in the hydrocarbon determines the final form of the gel. In general, the higher the copolymer content, the stiffer the gel. Additionally, the higher amount of triblock, radial block and/or multiblock copolymer in the polymer blend, the stiffer the blend gel. The gels under the present invention range from thin to stiff, as desired, and are generally transparent gels until opaque additives are added thereto.

Product formation is achieved from block copolymers which will form three-dimensional networks or gels through physical crosslinks. Crosslinking in these block copolymers occurs due to the formation of sub-microscopic particles of a particular block, referred to as domains. Crosslinking of the insoluble domains can be obtained by factors affecting the crosslink density of the networks including length of insoluble block domains, length of soluble block domains, and the number of crosslinkable sites. For example, branched or star polymers and other multiblock copolymers will have more crosslinks than triblock or diblock polymers. The type of solvent or plasticizer to which the blocks are subjected will also affect these characteristics.

Certain gels exhibit syneresis wherein the separation of liquid from the gel by contraction occurs by virtue of the concentration of the insoluble block present in the triblock copolymer. The higher the concentration of the insoluble block, as exemplified by styrene, the more phase separation and crosslinking will occur. However, according to this invention, the amount of syneresis which occurs can be controlled by mixing such systems with diblock, triblock, radial block and/or multiblock copolymers which do not exhibit syneresis.

The composition of the invention has the advantage in that the consistency of the gel can be varied from a soft, flowable gel to a stiff gel depending upon the composition of the polymer blend and, as such, is suitable for uses that cannot be made using particulates and non-self supporting gels or other dispersions of solid particles.

In a particularly preferred embodiment of the invention, the gel comprises a blend of a Kraton® triblock copolymer and a Kraton® diblock copolymer, as described herein, in combination with a hydrocarbon, particularly natural or synthetic hydrocarbons which are known as having a smooth homogeneous consistency. It is preferred under the present invention that the end block to ethylene and butylene center block ratio in the triblock copolymer be less than 31:69. The gels of the invention are prepared by blending into the hydrocarbon one or more triblock, radial block and/or multiblock copolymers, or mixtures thereof, and optionally one or more diblock copolymers, each in the desired amount.

In one method of preparation, the hydrocarbon is first heated to from about 65° C. to about 170° C. One or more triblock, radial block and/or multiblock copolymers, or mixtures thereof, and optionally one or more diblock copolymers, each in the desired amount, is then slowly added to the hot hydrocarbon with agitation. The temperature of the mixture is held for a time sufficient to dissolve the copolymer or blend thereof in the hydrocarbon. Mixing may be carried out in any conventional manner,and is again preferred at this stage. The polymer mix is sufficiently dissolved, generally in about 30 to 120 minutes, when the hydrocarbon/polymer mixture becomes clear and homogeneous.

The solid or liquid to be dispersed therein is then generally added to the gel in the desired amount at the cooling stage, although in the instance of certain substances, most notably solids, the addition may be advantageously prior to heating. The composition is then allowed to further cool to form a gel.

In another embodiment of the invention, the hydrocarbon is first heated to from about 65° C. to about 170° C., at which point the copolymer mix is added to the desired weight percent as set forth herein. After sufficient time for the copolymer to melt in the hydrocarbon, the composition is then allowed to cool to form a gel. During cooling, the solid or liquid to be dispersed therein is generally added. Similar variations of the method of the invention and known to the skilled person in light of the present disclosure are within the scope of the present invention.

The non-aqueous, gels of this invention may also contain about 0.01 up to about 5.0 weight percent of one or more conventionally employed additives such as stabilizers, antioxidants, colorants, and the like to an extent not affecting or decreasing the desired properties of the gel, namely the ability of the gel to perform its desired function. With respect to antioxidants, specific reference is made to BHT, which is generally employed in amounts of about 0.02 weight percent.

The following examples are presented to illustrate the invention, and the invention is not to be considered as limited thereto. In the examples, parts are by weight per 100 weight parts of the composition (i.e. weight percent), unless otherwise indicated.

In these examples, the diblock and triblock polymers used are the preferred Kraton® polymers 1702 and 1650 described above and obtained from Shell Chemical Company. Drakeol 7 is white mineral oil.

EXAMPLE 1

Identical makeup foundations were prepared (oil-in-water emulsions), one using a gel based on Drakeol 7 (Gel 1: prepared from 8.30 wt.% Kraton 1702 and 0.40 wt.% Kraton 1650) and one using Drakeol 7. After centrifugation for 1 hour at 7000 rpm, the top and bottom sections of the centrifuged samples were analyzed for iron (pigments are iron oxides). In the makeup prepared with the gel, no difference in iron content was seen. Thus, the pigments did not separate. In the makeup prepared with Drakeol 7, 54% more iron was found in the bottom section than the top, thus indicating that the pigment in this makeup separated upon centrifugation.

EXAMPLE 2

A sample of 30% titanium dioxide in a mineral oil gel was prepared (30.00 wt.% titanium dioxide +3.00 wt.% Kraton 1702+0.15 wt.% Kraton 1650+66.85 wt.% Drakeol 7). This sample had a nice creamy consistency and showed no separation over time.

EXAMPLE 3

Samples of 10 wt.% titanium dioxide (different samples, different suppliers) in the Gel of Example 1 were prepared and centrifuged at 4000 rpm for 30 minutes. Analysis of the top and bottom sections for titanium oxide showed no separation in any of the samples.

EXAMPLE 4

Talc was used as a mimic for agricultural actives. Talc was added at 30 vol % (=11.5 wt.%) to Gel 2 (prepared from Drakeol 7, 4.50 wt.% Kraton 1702, and 0.25 wt.% Kraton 1650) and Gel 3 (prepared from Drakeol 7, 6.50 wt.% Kraton 1702, and 0.40 wt.% Kraton 1650). After 18 days at 52° C., no separation of the talc was seen.

EXAMPLE 5

Again, 11.5 wt.% talc was used in different gels along with surfactants. These surfactants may be required if a blend of the gel and active is diluted with water to make a milky emulsion which is sprayed on a field of crops. The blends shown in the following table were prepared with no separation seen in any sample after 14 days at 52° C.

TABLE

|  | SAMPLE A | SAMPLE B | SAMPLE C | SAMPLE D |
| --- | --- | --- | --- | --- |
| Gel 1 | 70.87 wt % | — | 66.31 wt % | — |
| Gel 4 | — | 70.87 wt % | — | 66.31 wt % |
| Talc | 11.48 | 11.48 | 11.47 | 11.47 |
| Igepal CO-610 | 10.59 | 10.59 | — | — |
| Arlacel 83 | 7.06 | 7.06 | — | — |
| Span 80 | — | — | 4.44 | 4.44 |
| Tween 80 | — | — | 17.78 | 17.78 |

(Note: Gel 4 consists of Drakeol 7 + 7.60 wt % Kraton 1702 + 0.40 Kraton 1650.)

EXAMPLE 6

To a blend of 50 wt% gelled mineral oil was added 50 wt% coated zinc oxide (Z-Cote HP 1, from sunSmart, Inc.). The resulting suspension of zinc oxide was smooth and creamy, and showed no signs of particle agglomeration, settling, or separation, even after storage at 52° C. for 6 months, and after several freeze-thaw cycles.

EXAMPLE 7

Gel 2 was prepared from isohexadecane (Permethyl 101A, from Presperse). This gel (40 wt%) was mixed with 60 wt% Z-Cote HP 1 and gave a product in which the zinc oxide particles did not clump or settle.

EXAMPLE 8

Gel 2 was prepared from hydrogenated polyisobutene (Panalane L-14E, from Amoco Chemical) and was mixed at 50 WT% with Z-Cote HP 1 (at 50 wt%). Stabilities similar to those seen in Examples 6 and 7 were noted.

EXAMPLES 9–11

Gel 2 was prepared using (a) isohexadecane, (b) isododecane (Permethyl 99A, from Presperse), and (c) polydecene (Puresyn 4, from Mobil) In each example, 50 wt% of Z-Cote HP 1 was blended with 50 wt% of the gel. Agglomeration was not seen in any example, and each suspension had a smooth consistency with no signs of separation.

In the above Table, Igepal CO-610, Aracel 83, Span 80, and Tween 80 are surfactants available commercially under these tradenames.

While the above examples show that the gels of the invention are useful for suspension of solid particles in an emulsion, it should also be understood that the gels of the invention are also excellent suspending and dispersing agents when formulated into water and oil emulsions. Such emulsions include oil-in-water emulsions, water-in-oil emulsions, and multiple emulsions such as water-in-oil-in-water emulsions.

What is claimed is:

1. A hydrocarbon gel composition having at least one hydrocarbon-insoluble solid dispersed therein, said composition being non-aqueous and comprising:
   (a) from about 20 to about 95 weight percent of a hydrocarbon, or a hydrocarbon comprising one or more hydrocarbon-soluble substances, said hydrocarbon having 5 to 60 carbon atoms;
   (b) from about 0.1 to about 50 weight percent of a polymeric gel component, said polymeric gel component comprising one or more diblock copolymers in admixture with one or more triblock, radial block or multiblock copolymers, or a mixture thereof, wherein each of said diblock, triblock, radial block and multiblock copolymers contain at least two thermodynamically incompatible segments, said polymeric gel component consisting of from about 0 to about 100 weight percent diblock copolymer and from about 100 to about 0 weight percent of triblock, radial block or multiblock copolymer, with the proviso that, when the polymeric gel component comprises triblock copolymer, the polymeric gel component contains about 0.1 to about 25 weight percent triblock copolymer; and
   (c) from about 0.1 to about 75 weight percent of a suspended or dispersed component, the suspended or dispersed component comprising at least one hydrocarbon-insoluble solid;
   wherein the suspended or dispersed component remains uniformly suspended or evenly dispersed within the hydrocarbon gel composition.

2. A gel composition according to claim 1, wherein the hydrocarbon-insoluble solid is selected from the group consisting of agricultural substances and veterinary medicines.

3. A gel composition according to claim 2, wherein the non-hydrocarbon soluble solid is an agricultural substance selected from the group consisting of hydrocarbon-insoluble pesticides, hydrocarbon-insoluble fungicides and hydrocarbon-insoluble herbicides.

4. A gel composition according to claim 2, wherein the hydrocarbon-insoluble solid is a veterinary medicine selected from the group consisting of dewormers, vaccines, and other medicines.

5. A gel composition according to claim 1, wherein the hydrocarbon-insoluble solid is a personal care ingredient.

6. A gel composition according to claim 5, wherein the personal care ingredient is selected from the group consisting of pigments, sunscreens, and sunblocks.

7. A gel composition according to claim 1 in the form of a soft, flowable gel.

8. A gel composition according to claim in the form of a stiff, self-supporting gel.

9. A water-in-oil emulsion comprising a gel composition according to claim 1 and sufficient water to form said water-in-oil emulsion, and one or more emulsifying agents.

10. An oil-in-water emulsion comprising a gel composition according to claim 1 and sufficient water to form said oil-in-water emulsion, and one or more emulsifying agents.

11. A gel composition according to claim 1, wherein the polymeric gel component comprises a blend of an S-EB-S triblock copolymer and a S-EP diblock copolymer.

12. A gel composition according to claim 1, wherein the component (c) comprises a hydrocarbon-insoluble solid selected from the group consisting of: zinc oxide, coated zinc oxide, surface-treated zinc oxide, titanium dioxide, surface-treated titanium dioxide, hydrocarbon-insoluble phosphorescent substances, molybdenum oxide, zinc sulfide, copper-doped zinc sulfide, graphite, explosive materials, air-sensitive chemicals or reagents, moisture-sensitive chemicals or reagents, boron nitride, iron oxides, talc, mica, hydrocarbon-insoluble plastics, hydrocarbon-insoluble polymers and polymeric materials, hydrocarbon-insoluble phosphorescent or fluorescent materials, hydrocarbon-insoluble medical materials, glass, clays, gums, capsules containing various ingredients, starch, modified starches, and mixtures thereof.

13. A composition according to claim 1, wherein the hydrocarbon-insoluble solid is a hydrocarbon-insoluble medical material selected from the group consisting of antibacterials, antibiotics, and anesthetics.

14. A composition according to claim 12, wherein the hydrocarbon-insoluble solid is an explosive.

15. A composition according to claim 12, wherein the hydrocarbon-insoluble solid is at least one air-sensitive chemical or reagent, or at least one moisture-sensitive chemical or reagent.

16. A composition according to claim 12, wherein the hydrocarbon-insoluble solid is selected from the group consisting of zinc oxide, coated zinc oxide, surface-treated zinc oxide, titanium dioxide, surface-treated titanium dioxide, molybdenum oxide, zinc sulfide, copper-doped zinc sulfide, graphite, boron nitride, iron oxides, talc, mica, glass, clays, gums, starch, modified starches, and mixtures thereof.

17. A composition according to claim 12, wherein the hydrocarbon-insoluble solid is selected from the group consisting of hydrocarbon-insoluble phosphorescent substances, hydrocarbon-insoluble plastics, hydrocarbon-insoluble polymers and polymeric materials, and capsules containing various ingredients.

18. The composition according to claim 1, wherein the hydrocarbon-insoluble substance in subpart (c) comprises iron oxides, titanium dioxide or talc.

* * * * *